(12) United States Patent
Zuckerman et al.

(10) Patent No.: US 10,157,536 B2
(45) Date of Patent: Dec. 18, 2018

(54) DISPATCH MANAGEMENT PLATFORM FOR NURSE CALL SYSTEM

(71) Applicants: Yair Zuckerman, Lincolnwood, IL (US); Nathaniel Robeson, Chicago, IL (US)

(72) Inventors: Yair Zuckerman, Lincolnwood, IL (US); Nathaniel Robeson, Chicago, IL (US)

( * ) Notice: Subject to any disclaimer, the term of this patent is extended or adjusted under 35 U.S.C. 154(b) by 0 days.

(21) Appl. No.: 15/671,969

(22) Filed: Aug. 8, 2017

(65) Prior Publication Data

US 2018/0082573 A1    Mar. 22, 2018

Related U.S. Application Data

(60) Provisional application No. 62/494,378, filed on Aug. 8, 2016.

(51) Int. Cl.
| | |
|---|---|
| *G08B 25/00* | (2006.01) |
| *G08B 21/18* | (2006.01) |
| *G08B 25/01* | (2006.01) |
| *A61B 5/00* | (2006.01) |

(52) U.S. Cl.
CPC ............ *G08B 25/001* (2013.01); *A61B 5/747* (2013.01); *G08B 21/182* (2013.01); *G08B 25/016* (2013.01)

(58) Field of Classification Search
CPC ... G08B 25/001; G08B 21/182; G08B 25/016
USPC ..................................................... 340/286.7
See application file for complete search history.

(56) References Cited

U.S. PATENT DOCUMENTS

| | | | | |
|---|---|---|---|---|
| 5,561,412 A | * | 10/1996 | Novak | A61G 12/00 340/286.06 |
| 5,822,544 A | | 10/1998 | Chaco | |
| 8,775,196 B2 | * | 7/2014 | Simpson | G06F 19/3418 705/2 |
| 9,240,120 B2 | | 1/2016 | Girardeau | |
| 9,465,916 B2 | | 10/2016 | Girardeau | |
| 9,690,538 B1 | * | 6/2017 | Doyle, III | G06F 3/1454 |
| 2006/0143044 A1 | | 6/2006 | Conry | |
| 2007/0080801 A1 | * | 4/2007 | Weismiller | A61B 5/411 340/539.13 |
| 2008/0164998 A1 | * | 7/2008 | Scherpbier | G06Q 10/06 340/539.13 |

(Continued)

*Primary Examiner* — Hirdepal Singh
(74) *Attorney, Agent, or Firm* — Gordon Feinblatt LLC; Royal W. Craig

(57) ABSTRACT

A dispatch management computer system that integrates with an existing nurse call system for clinical workflow optimization and to create accountability for patient satisfaction and outcomes. The system integrates a "quarterback" (e.g., dispatcher) tablet with a custom dispatch application that presents a floor plan for tracking the RTLS position of staff members and to provide a visual indication of which room and bed the call originated from. When a patient requests assistance, the QB application presents an assessment of the patient needs and, if further assistance is required, provides the dispatcher tools for real time assignment of the appropriate staff member and dispatch to begin the task within a predetermined amount of time required to complete the task allocated. The system enables the prompt assignment of staff personnel and assures that a patient receives prompt staff attention.

26 Claims, 10 Drawing Sheets

(56) References Cited

U.S. PATENT DOCUMENTS

| | | | |
|---|---|---|---|
| 2009/0313046 A1* | 12/2009 | Badgett | G06F 19/327 |
| | | | 705/3 |
| 2010/0001838 A1* | 1/2010 | Miodownik | G06Q 10/06 |
| | | | 340/10.1 |
| 2012/0253836 A1 | 10/2012 | Nolte | |
| 2012/0310664 A1 | 12/2012 | Long | |
| 2014/0218202 A1* | 8/2014 | Wilson | A61B 5/747 |
| | | | 340/686.6 |
| 2014/0244298 A1 | 8/2014 | Robinson | |
| 2015/0302539 A1* | 10/2015 | Mazar | G08B 21/0211 |
| | | | 705/3 |
| 2016/0300178 A1* | 10/2016 | Perry | G06Q 10/063112 |
| 2017/0004264 A1* | 1/2017 | Girardeau | G08B 25/10 |
| 2017/0287316 A1* | 10/2017 | Wildman | G08B 25/10 |

* cited by examiner

| | | | | |
|---|---|---|---|---|
| | Angelita Johnson Nurse<br>5th Floor 513514 • Online<br>☆ Mobile ID: 133 Tag ID: 156544 | ⌚ ⬆ | Available<br>Task unassigned<br>Task not started | |
| | HK %th Floor Housekeepers<br>5th Floor Lobby • Online<br>☆ Mobile ID: 88 Tag ID: 143506 | ⬆ | Available<br>Task unassigned<br>Task not started | |
| | Rashaan Stewart Nurse<br>5th Floor 501 502 • Online<br>☆ Mobile ID: 224 Tag ID: 154368 | ⬆ | Available<br>Task unassigned<br>Task not started | |
| | Angelito Obra Nurse Stewart Nurse<br>7th Floor 703 704 • Online<br>☆ Mobile ID: 58 Tag ID: 140392 | ⬆ | Available<br>Task unassigned<br>Task not started | |
| | Adria Cullins CNA<br>Out of range   Offline<br>☆ Mobile ID: 124 Tag ID: 149574 | | Available<br>Task unassigned<br>Task not started | |
| | Amber Green CNA<br>Out of range   Offline<br>☆ Mobile ID: 241 Tag ID: 143568 | | Available<br>Task unassigned<br>Task not started | |
| | Angel Thomas Quarterback<br>Out of range   Offline<br>☆ Mobile ID: 250 Tag ID: 140436 | | Available<br>Task unassigned<br>Task not started | |
| | Angela Hurst CNA<br>Out of range   Offline<br>☆ Mobile ID: 220 Tag ID: 164933 | | Available<br>Task unassigned<br>Task not started | |
| | Anna Genaro CNA<br>Out of range   Offline<br>☆ Mobile ID: 126 Tag ID: 148772 | | Available<br>Task unassigned<br>Task not started | |
| | Antoinette Mills CNA<br>Out of range   Offline<br>☆ Mobile ID: 217 Tag ID: 143497 | | Available<br>Task unassigned<br>Task not started | |

🔍 Enter staff name   ⬆ ⬇

Fig. 5

Call Summary Report

From: 1/9/2017 To: 1/15/2017   Call Time Threshold set to: 60 Seconds

| Date | Floor | Shift | Calls | | | Assigns | | | Tasks | | | Totals | |
|---|---|---|---|---|---|---|---|---|---|---|---|---|---|
| | | | Total | Under | Over | Avg Time | Under | Over | Avg Time | Under | Over | Avg Time | Avg Time | Score |
| 1/9/2017 Monday | 5th Floor | 10P 6A | 69 | 34 | 35 | 1:29 | 57 | 12 | 2:36 | 31 | 8 | 2:27 | 6:32 | |
| | | 2P 10P | 143 | 53 | 90 | 2:44 | 91 | 52 | 5:08 | 56 | 38 | 2:45 | 10:37 | |
| | | 6A 2P | 144 | 94 | 50 | 1:16 | 102 | 42 | 2:48 | 42 | 59 | 1:54 | 5:58 | |
| | | *Shift Total* | *356* | *181* | *175* | *1:54* | *250* | *106* | *3:42* | *129* | *105* | *2:21* | *7:56* | |
| | 6th Floor | 10P 6A | 3 | 3 | 0 | 0:43 | 3 | 0 | 0:35 | 2 | 1 | 1:43 | 3:01 | |
| | | 2P 10P | 63 | 34 | 29 | 2:12 | 44 | 19 | 4:03 | 10 | 13 | 1:59 | 8:14 | |
| | | 6A 2P | 66 | 37 | 29 | 2:08 | 47 | 19 | 3:53 | 12 | 14 | 1:58 | 7:59 | |
| | | *Shift Total* | | | | | | | | | | | | |
| | *Floor Total* | | *422* | *218* | *204* | *1:56* | *297* | *125* | *3:44* | *141* | *119* | *2:17* | *7:57* | |
| 1/10/2017 Tuesday | 5th Floor | 10P 6A | 43 | 12 | 31 | 2:27 | 28 | 15 | 3:20 | 20 | 9 | 2:40 | 8:26 | |
| | | 2P 10P | 160 | 78 | 82 | 3:19 | 77 | 83 | 8:32 | 48 | 55 | 2:56 | 14:46 | |
| | | 6A 2P | 141 | 105 | 36 | 0:57 | 65 | 76 | 6:46 | 39 | 33 | 2:19 | 10:02 | |
| | | *Shift Total* | *344* | *195* | *149* | *2:14* | *170* | *174* | *7:09* | *107* | *97* | *2:39* | *12:02* | |
| | 6th Floor | 10P 6A | 2 | 2 | 0 | 0:12 | 2 | 0 | 1:56 | 0 | 0 | 0:0 | 2:08 | |
| | | 2P 10P | 69 | 51 | 18 | 1:00 | 49 | 20 | 3:23 | 28 | 15 | 1:49 | 6:12 | |

FIG. 12

DISPATCH MANAGEMENT PLATFORM FOR NURSE CALL SYSTEM

CROSS-REFERENCE TO RELATED APPLICATION(S)

The present application derives priority from U.S. Provisional Patent Application 62/494,378 filed 8 Aug. 2016.

BACKGROUND OF THE INVENTION

1. Field of the Invention

The present invention relates to a computer system and method for responding to nurse calls in a healthcare setting and, more particularly, to a nurse call assurance platform for clinical workflow optimization that creates accountability for patient satisfaction and outcomes.

2. Description of the Background

Hospitals, outpatient facilities, and nursing facilities all share a common need for improving the time it takes in responding to the patient needs and requests. Because of the current procedures. Typically patients will use a nurse call button to summon assistance. In most facilities this triggers a visual indication over the patient's room and a call indication at the nurse station. However, nursing staff may be busy attending other patients or otherwise be preoccupied. They may not be aware of the call and there is no assurance that the patient will be attended to in a timely manner. Timely attention can be critical in an emergency situation.

The average industry response today to a nurse's call is approximately 5 minutes but can be as high as 30 minutes or more especially when available staff is busy. This is major source of patient frustration and dissatisfaction. Several studies also show longer call response times contribute significantly to the risk of falling.

Part of the problem is that providers do not use their nurses efficiently. Typically, a group of nurses is stationed at a central station, and each nurse will service a set area by continuously rotating through the rooms assigned in that area to check each patient's condition. This approach has several disadvantages. For one, a nurse may be checking on one patient when an emergency occurs to another patient, and the alarm to the central station goes unanswered for a time. Modern nurse call systems provide for two-way communication between a patient and a nurse to avoid this, but the existing approach of assigned nurse rounds is not efficient.

There have been prior efforts to automate the nurse call process as it currently exists.

For example, U.S. Pat. No. 9,240,120 to Girardeau et al. (Hill-Rom) issued Jan. 19, 2016, U.S. Pat. No. 9,465,916 to Girardeau et al. (Hill-Rom) issued Oct. 11, 2016, and United States Patent Application 20170004264 by Girardeau et al. (Hill-Rom) published Jan. 5, 2017 are all drawn to a system to keep track of rounding intervals for caregivers to determine whether the caregivers successfully complete their rounds in a timely manner for their assigned patients. The system uses a real time location system (RTLS) that tracks locations of caregivers. A central server facilitates and tracks nurse calls and system alerts to insure that a caregiver is adequately monitoring patients under their care, and particularly to ensure that the caregiver remains in the patient's room for a threshold period of time. However, there is no input from any other users, aside from the nursing staff, nothing from the patient/resident about the call/request, and no capability for integration with other enterprise systems such as records, payroll, etc. The system simply determines whether nurses complete their rounds in a timely manner for their assigned patients.

United States Patent Application 20060143044 by Conry et al. (General Electric) shows a health care resource scheduling system based on performance data for any relevant resources including personnel, service providers, and so forth.

U.S. Pat. No. 5,561,412 to Novak et al. (Hill-Rom, Inc.) issued Oct. 1, 1996 discloses a patient/nurse call system which prioritizes and stores the calls. Hall units outside patient rooms identify the rooms from which the calls originate and the type of call. Each patient station allows selective retrieval and display of unanswered calls. Nurse-worn badges transmit pulse-coded infrared signals which are received by receivers at the patient stations. Receipt of a nurse's infrared signal at a room station automatically cancels a patient call originating from the room and display thereof by the respective hall unit, while actuating a display to indicate nurse presence.

Similarly, U.S. Pat. No. 5,822,544 to Chaco et al. (Hill-Rom) issued Oct. 13, 1998 shows a patient care and communication system using RTLS badges attachment to individual personnel, a central station for determining the location of personnel within a health care facility, a patient station (door sign) with a staff-in-room indicator. When the central station determines the location of personnel in a patient room, the central station actuates the indicator assembly.

United States Patent Application 20140244298 by Robinson et al. (Hill-Rom) published Aug. 28, 2014 shows an electronic room sign system that combines electronic medical records (EMR) with a real time locating system (RTLS). The electronic room sign is mounted adjacent a doorway of a room of a patient and a server signaling the display to display information based on information received by the server from the EMR system and from the RTLS.

United States Patent Application 20120310664 by Long et al. (Proventix) published Dec. 6, 2012 shows a system and method for monitoring compliance with a workflow procedure in a hospital or other health care facility comprising a computer device to keep track of rounds (pars. 15-16), a real time locating system for tracking location of a plurality of caregivers, and a plurality of graphical displays in communication with the computer device (FIGS. 5-6) for displaying patients and reminders (FIG. 6, par. 22—patient John Doe, urgent indicator and auditory alert).

United States Patent Application 20120253836 by Nolte et al. published Oct. 4, 2012 shows an assignment system that takes a list of clinicians, a list of patients, and an estimate of the amount of resources required to provide care to a patient.

There are also a number of commercially-available nurse call systems. For example, the NaviCare® system marketed by Hill-Rom Company, Inc. includes software that provides a tabular display of the status of patients, tasks that need to be performed, patient information, status of rooms, patient location, and other information at the various monitoring stations or displays located throughout the hospital. The NaviCare® 5.2 system allows medical staff to track the status of patients as the patients move throughout the hospital. In the NaviCare® 5.2 system, many of the various tasks that need to be performed, information about patients, and other information are represented by icons on the displayed tables.

FIG. 1 is a prior art healthcare provider network 10 that includes a workflow system (WFS) server 14, a data storage device 16, and one or more client PCs 18. Server 14 may be coupled to hospital network 20. A nurse call system 24 includes a nurse call server 26 and associated client PC's 28. There is also a location server 30, and an interactive voice recognition (IVR) server 32. Tracking tags 42 may be mounted to pieces of equipment or carried by nurses. Location server 30 executes software to track these tags 42. Server 30 associates the unique ID data from the tags 42 with ID data, such as a serial number, of the corresponding unit 40 which receives the wireless transmission from the tags 42. There is also a pager system 60 which is with pagers 62 carried by nurses. Server 14 and PC's 18 execute workflow software that has all of the functions and features of the Hill-Rom™ Navicare® 5.2 system software, including determining the closest nurse to a room issuing a call, and actuates that nurse's pager.

Unfortunately the foregoing references are all concerned with automating, monitoring and enforcing an existing workflow. What is needed is a new and improved workflow model, and a new and improved system for implementing the new model on a conventional nurse call system as described above.

The present inventors do this with a novel "Quarterback" approach to provide patient care. Rather than a nurse call switchboard at the nurse station, the present system requires appointment of a "Quarterback", e.g., a designated staff member responsible for monitoring and attending to all patient requests for assistance in a timely manner. Given this new business model, what is needed is a computerized nurse call assurance platform that gives the quarterback the tools and automation to achieve clinical workflow optimization, and to assume full accountability for patient satisfaction and outcomes. The present invention gives the dispatcher (quarterback) the tools and automation to quickly assess what a patient needs, determine if further assistance is required, select and assign an appropriate staff member, dispatch that staff member to begin the task with a known allotment of time required to complete the task, and monitor results. If the task is not completed in a timely manner, the application notifies the dispatcher and provides detailed reports for investigation of the reason for the delay. All information regarding the call, task assignment, task completion, patient information, staff position and availability are displayed in the dispatcher's browser and statistical data is archived for reporting.

SUMMARY OF THE INVENTION

It is, therefore, a primary object of the present invention to provide a dispatch management platform for integration with an existing nurse call system for more efficient deployment of provider staff.

It is another object of the invention to provide a dispatch management platform as above that tracks and produces a new set of metrics for more efficient deployment of provider staff.

It is another object of the invention to increase the level of automation of the nurse dispatch process.

It is another object to provide a system that maintains an audit trail throughout the nurse call process.

These and other objects are herein accomplished by a dispatch management platform for integration with an existing nurse call system for clinical workflow optimization and to create accountability for patient satisfaction and outcomes. The present platform is a hardware and software solution that integrates smart devices (phones and tablets) and a Real Time Location System (RTLS) platform with existing nurse call system and medical records database, to enable the prompt assignment of staff personnel system that assures that a patient receives prompt staff attention. A "quarterback" (QB, e.g., dispatcher) is appointed and given a tablet with a custom application that presents a floor plan for tracking the position of staff members and to provide a visual indication of which room and bed the call originated from. The quarterback relies on staff members that wear an RTLS tracking badge with a unique ID number. The RTLS solution used relies on a combination of trilateration and fingerprinting to determine X-Y coordinates, plus Bluetooth low energy beacons which send fixed proximity information to mobile devices.

When a patient requests assistance, the QB application presents an assessment of the patient needs and, if further assistance is required, provides the QB dispatcher tools for real time assignment of the appropriate staff member and dispatch to begin the task within a predetermined amount of time required to complete the task allocated. The appropriate staff member for this is selected by their title, their location as shown in the floor plan, and their availability to begin the task. All tasks are displayed in a QB application Call Browser: the call room and bed number, timestamp of the call, time elapsed for attending and canceling the call, time elapsed to assign the task, the staff member assigned to the task, the task description, the time allocated to complete the task, the time elapsed for task completion, patient name and other patient information and total elapsed time.

The QB application is continuously running and keeps track of three timed stages each affecting the patient expected wait time:

1. Call: The time from when the patient activates the nurses call button, creates a custom call, or a scheduled custom call is triggered until that call button is cancelled.

2. Assign: The time from the call button cancellation until the task is assigned and the assigned staff physically starts the task. The QB can start the task timer (or staff member with the Nurse application when permitted by then QB, see below).

3. Task: The time it takes for the staff to complete the patient's needs.

If the task is not completed in a timely manner, the QB application Call Browser notifies the dispatcher who can then investigate the reason for the delay. All information regarding the call, task assignment, task completion, patient information, staff position and availability are displayed in both the QB application Call Browser and Nurse Application Browser, and visually indicated on the floor plan. All statistical data is archived for reporting. A variety of management reports are available. In addition, other system features include asset tracking, temperature monitoring, etc.

BRIEF DESCRIPTION OF THE DRAWINGS

Other objects, features, and advantages of the present invention will become more apparent from the following detailed description of the preferred embodiments and certain modifications thereof when taken together with the accompanying drawings in which:

FIG. 5 is a screen print of the staff browser.

FIG. 12 is a screen print of an exemplary Call Summary Report.

DETAILED DESCRIPTION OF THE PREFERRED EMBODIMENT

The present invention is a nurse call dispatch platform for workflow optimization of the patient nurse call process that creates accountability for patient satisfaction and outcomes.

Figure 1:
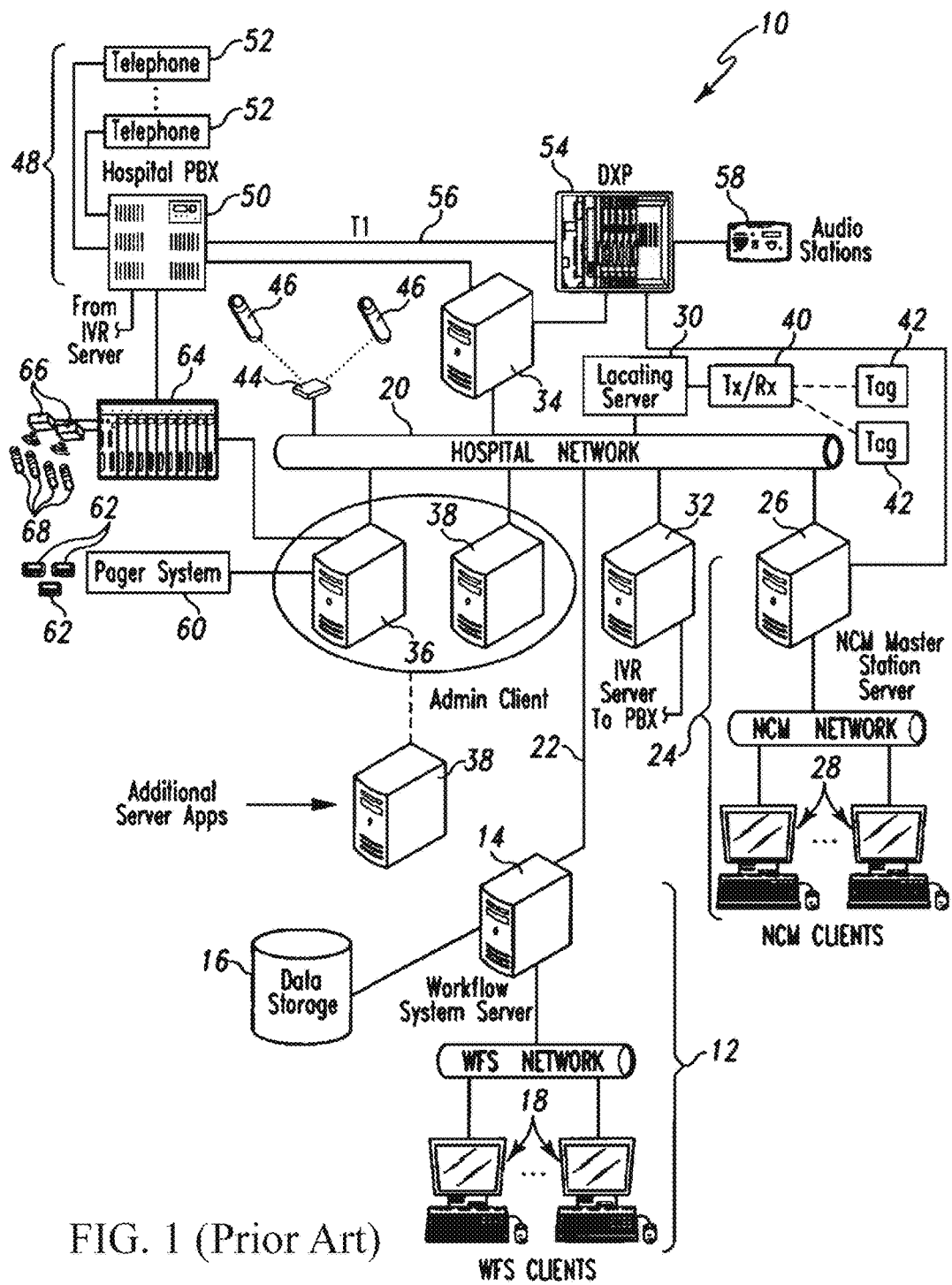
FIG. 1 is an illustration of a prior art hospital network and nurse call system.
Figure 2:
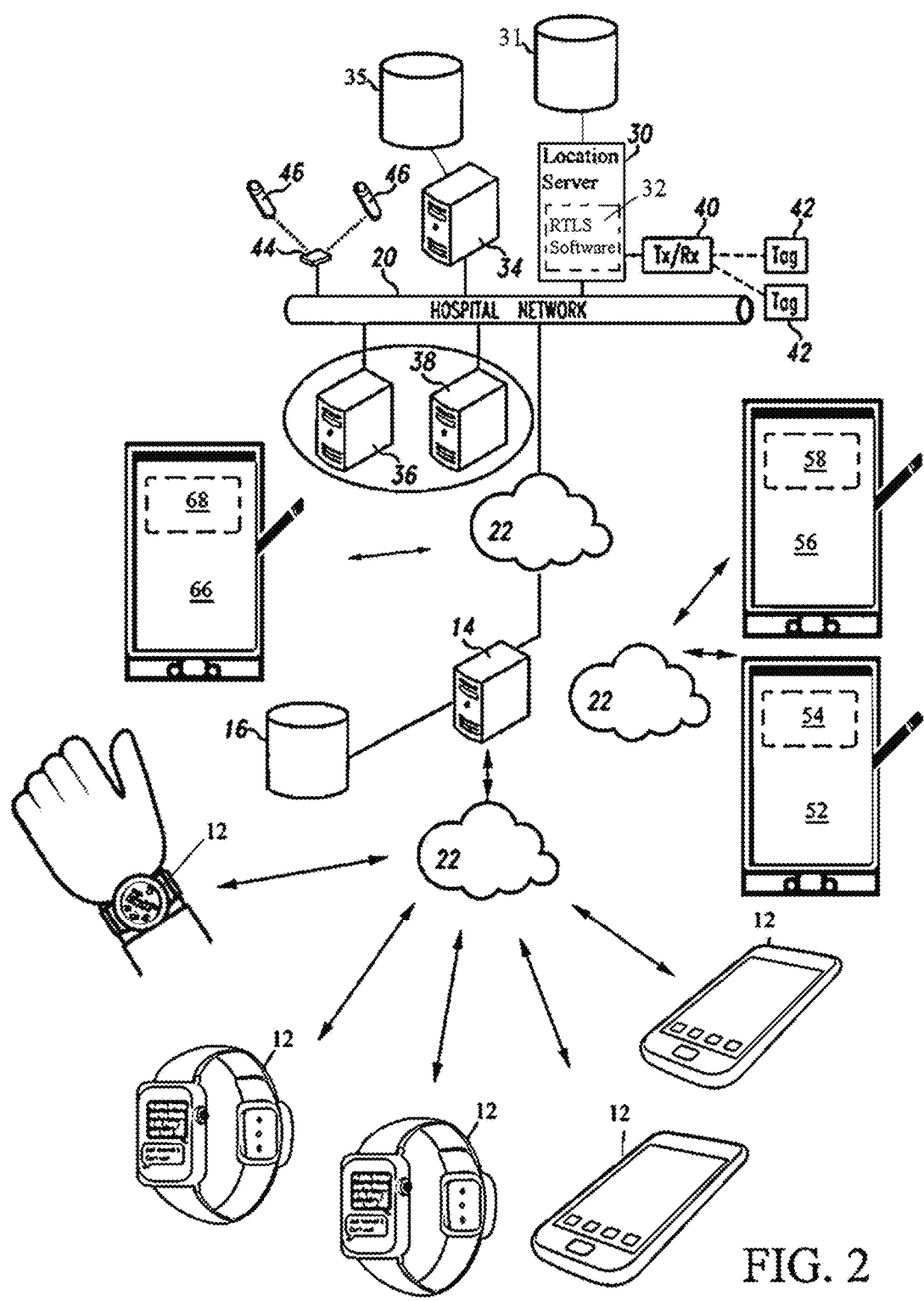
FIG. 2 is an illustration of the hardware architecture according to the invention.

FIG. 2 is an illustration of the hardware architecture of the present invention integrated with an existing nurse call system such as shown in FIG. 1, the latter typically including a distributed client-server hardware architecture as typically maintained at a healthcare facility. More specifically, the existing architecture may include a nurse call server 14 coupled to hospital network 20, and an RTLS location server 30 in communication with tracking tags 42 mounted to pieces of equipment or carried by nurses. Location server 30 executes software to track these tags 42. Location server 30 associates unique ID data from the tags 42 with ID data, such as an ID number of the carrying nurse.

In accordance with the workflow of the present invention one person is assigned to the dispatch quarterback (QB) role, and he/she is provided with a QB tablet 52 that executes a QB software application 54 as will be described. The QB tablet 52 is in wireless communication with nurse call server 14 and in communication with hospital network 20 and RTLS location server 30 via a reliable facility Wi-Fi network 22 with an internet backbone connection.

The QB manages task assignments to a staff of nurses or the like, and the dispatches are made through a plurality of portable communications devices (PDAs) 12 worn or carried by each nurse or staff member. PDAs 12 are preferably wearable devices but may be any portable text-messaging capable device including smart watches or smart phones each running a StaffWear Application. PDAs 12 are capable of selectively and proactively consolidating SMS/MMS messaging in real time as messages are sent via their native text messaging application, into nurse call server 14. Groups of PDAs 12 are connected to QB server 14 and to hospital network 20 via a reliable facility Wi-Fi network 22 with an internet backbone connection. The QB server 14 hosts a resident routing database which stores data authentication and verification information (usernames and passwords) correlating to registered participants including nurses.

The hospital network 20 preferably includes a medical records repository comprising a database server 34 in communication with non-transitory computer memory 35, which may be local or any distributed storage array. The database server 34 runs database management software to provide database services to client-server network 20. Database management systems frequently provide database server functionality, and some DBMSs (e.g., MySQL) rely exclusively on the client-server model for database access. Thus, medical records repository preferably hosts a network database on the non-transitory computer memory 35, preferably an SQL server database, and even more preferably Microsoft™ SQL Server I. Other examples of suitable database servers are MySQL (a popular open source database), Oracle™, DB2™, Informix™, Ingres™, and SQL Server™. The medical records repository 34, 35 shown in FIG. 2 is a part of the local client/server environment 20, but may alternately be a cloud-based repository connected directly to the internet.

The software method of the invention, delivered through the foregoing network, is a nurse call dispatch platform for clinical workflow optimization that facilitates deployment and tracking of nurses using PDAs 12, and creates accountability for patient satisfaction and outcomes.

As above, a "quarterback" or QB is appointed and given the QB tablet 52 with QB application 54. The QB relies on nurses and staff members to wear an RTLS tracking badge 42 with a unique ID number. The Location Server 30 can host most any commercially-available RTLS or custom beacon solution. Currently, there are three localization techniques: proximity, trilateration (or, range-based) and fingerprinting (FP) [Hui L., Darabi H., Banerjee P., Jing L., Survey of wireless indoor positioning techniques and systems, IEEE Trans. Syst. Man Cybern. C Appl. Rev. 2007; 37:1067-1080] Some commercially available solutions provide a hybrid trilateration and fingerprinting capability such as the Purelink™ embedded RTLS solution. Others use send fixed proximity information to mobile devices. In an embodiment the present system may rely on a combination of trilateration and fingerprinting to determine X-Y coordinates, plus Bluetooth low energy beacons which send fixed proximity information to mobile devices.

Each personal badge or asset tag 42 is actually a small Bluetooth transmitter that sends a burst of information 1 to 5 times per second. This information contains a unique badge ID, battery level, and other information depending on the type of badge 42. In a preferred embodiment the present system employs temperature badges 42 able to additionally transmit ambient temperature, motion badges 42 meant for wear by patients to detect movement for security, and optical asset tags 42 able to detect door or window opening/closing.

The system performs accurate location within 3.5 meters (All RF systems are susceptible to RF interference). In addition to trilateration and fingerprinting, the nurse tracking transmitter/receiver combinations 40 provide simple Bluetooth proximity indications when a badge 42 is within Bluetooth range to supplement RTLS needs.

Importantly, for present purposes the embedded RTLS solution is configured to run on a client-server model using RTLS server software 32 resident at location server 30, communicating with the QB application 54 on tablets 52. The RTLS server software 32 comprises a separate interface for each RTLS vendor database 31 that effectively translates the vendor data into a more concise format that includes all positioning information and is not vendor specific. Vendor-formatted data is converted to a generic SQL-based data format by separate cross-reference tables shown below which contain positioning and other information (i.e., MobileID, TagID, Staff Name or Asset Description, X and Y coordinates, Zone, Temperature etc.). There are five (5) separate cross-reference SQL tables as follows:

Staff

Assets

Temperature

Motion—e.g., for Patient movement or security

Optical—e.g., On doors to detect open and close

The vendor-to-SQL conversion is achieved in real-time by running one or more cross-reference applications (each responsible for and dedicated to one RTLS vendor) continuously on the nurse call server 14 file server (thereby lowering overhead as stated above). This method accommodates the use of any existing RTLS OEM-installed systems at a facility or even multiple vendor's RTLS platforms, all of which can be easily integrated, and no update coding is ever required to the QB application or Nurse application.

The present system continually calculates RTLS positioning for all staff members in real time. The requisite calculations are not done on each QB tablet 52 to avoid throughput that might otherwise load down the application. This is because all the data would need to be transferred from the location server 30 through the hospital network 20 to the QB server 14 and on to each QB tablet 52 and each nurse's PDA 12. In the present system the RTLS server software 32 actually runs constantly as a separate application on the location server 30, which is the same server 30 where the RTLS vendor database 34 data is stored. This way, all complex logic and data transfer need not be transmitted across the entire network. Instead, a pre-calculated subset of RTLS coordinate data is sent to the devices thereby decreasing the load and increasing throughput. Also, updates can be centrally made, as data tables and structures are not coded in each QB tablet 52 or nurse PDA 12.

A critical component of the present system 2 allows the QB to receive notification of nurse calls and cancels in real time from legacy systems such as VisionPro™, CodeAlert™ and Dukane™. To accomplish this, the present system includes a data interface designed to interface with legacy systems such as VisionPro™, CodeAlert™ and Dukane™. The data interface is an intercept application that runs continuously on the nurse call server 14 that intercepts each nurse call from the legacy system, cancels it, and instead sends a redirected nurse call via a TCP socket to each QB tablet 52 for each floor or unit. Note that for older legacy nurse call systems that do not have a digital interface (like old Dukane™), this entails a hardware and software solution to intercept the nurse calls, to cancel, and redirect. Of course, one skilled in the art will understand that there may be alternatives, such as using RTLS tags or beacons located in call boxes in each patient room to forward the calls and cancels. These would come in through the location server 30, but this is a file server that track the many tags 42 that may be present (multiple SQL databases are hosted on the location server 30 to provide support for RTLS).

Figure 3:
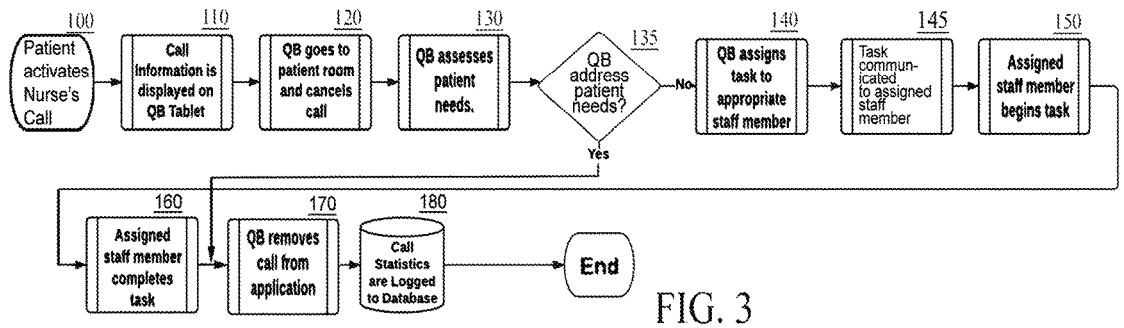
FIG. 3 is a flow chart of the workflow method of the invention.

FIG. 3 is a flow chart of the workflow method of the invention.

At step 100, a patient activates a nurse call. Patients may use wireless nurse call buttons 46 or their room console 44 to summon assistance, a patient tablet 66 running a patient application 68 as described below, or there may be automatic diagnostic sensors such as heart monitors or the like.

When a patient has requested assistance, at step 110 the QB server 14 compiles an assessment of the patient needs and presents this to the QB on tablet 52 via QB application 54 which displays a novel QB Call Browser. Each patient request for assistance or nurse call is displayed as an entry in a QB Call Browser queue. All tasks are displayed in the QB application Call Browser: the call room and bed number, timestamp of the call, time elapsed for attending and canceling the call, time elapsed to assign the task, the staff member assigned to the task, the task description, the time allocated to complete the task, the time elapsed for task completion, patient name and other patient information and total elapsed time.

At step 120 the QB proceeds to the patient's room and upon arrival deactivates the nurse call.

At step 130 the QB makes an initial assessment of the patient's needs. Of course, those need may range from another blanket, to a tripped heart monitor. If at step 135 the QB is personally able to handle the patient's needs then such is done. Even when the QB services the patient without other staff assistance being required, that call must still be canceled and is logged (all calls are always logged). The process jumps to step 170 (described below).

If, on the other hand, at step 140 the QB decides that further assistance is required, the QB application 54 Call Browser facilitates the assignment process by a succession of dispatch tools for real time assignment of the task to the appropriate nurse, based on based on title, their location, and their availability to begin the task within a predetermined amount of time allocated.

Tapping any nurse call entry in the QB Call Browser queue instantiates a Staff Browser to facilitate the QB's selection of a nurse to provide assistance. The Staff Browser (described in detail below) provides a sorted interactive list of all staff members that were assigned a tag 42. The QB can select the appropriate staff member directly.

Tapping any entry in the Staff Browser instantiates a Task Qualification Listing, e.g., a display of all tasks that the selected staff member is qualified to perform (based on employment level). This way the QB can ensure assignment of a nurse qualified for the task at hand. One skilled in the art should understand that this substep may be partially automated by the QB application 54 by prescreening the field of candidates by comparison of each employee's qualifications relative to the selected task(s).

At step 140 the QB assigns the task to the most appropriate nurse or staff member.

At step 145 the assignment is communication instantly via that nurse's PDA 12.

At step 150 the nurse begins the task.

At step 160 the nurse completes the task.

At step 170 the QB nurse removes the call from the queue.

The QB application 54 is continuously running and keeps track of three distinct timed stages each affecting the patient expected wait time:

1. Call: The time from when the patient activates the nurses call button, creates a custom call, or a scheduled custom call is triggered, until that call button is cancelled (steps 100-120).

2. Assign: The time from the call button cancellation until the task is assigned and the assigned staff physically starts the task. The QB or staff member can start the task timer (with the wear app when permitted by then QB. See below (Steps 120-150).

3. Task: The time it takes for the staff to complete the patient's needs (steps 150-160).

The QB application 54 maintains three separate timers for the three distinct phases: Call Timer; Assign Timer; and Task Timer. There are multiple timer indications indicative of the phase and time appearing on the QB application Call Browser 154:

The timer elapsed and remaining time (timer text colors change from green to yellow to red);

a radial progress bar shows percentage complete; and voice alerts provide audio warning If any phase is not completed within a predetermined time window, the QB application Call Browser 154 automatically notifies the QB dispatcher who can then investigate the reason for the delay.

Importantly, the QB application Call Browser 154 monitors the foregoing and provides notice, but also dynamically compensates based on circumstances. For example, during busy times, e.g., if there are more than three active calls that were not yet cancelled, the QB application Call Browser 154 is pre-programmed to compensate (follows a ruleset that presumes that the QB has not gone into these patient's rooms yet) and will automatically extend the standard time window (e.g., 30-60 seconds) to a greater vale value (e.g., 90-120 seconds) without invoking red flags or warning messages.

All information regarding the call, task assignment, task completion, patient information, staff position and availability are displayed in both the QB application 54 Call Browser on tablet 52 and on the Staff Wear Application on PDA 12. All event and time data is archived for reporting. As will be described a variety of management reports are available, and ancillary system features include asset tracking, temperature monitoring, etc.

The QB application 54 QB Call Browser 154 is a mobile application and may be implemented as standalone software program on tablet 52, but is more preferably a server-side program resident on WFS server 14 with a thin-client front end on tablet 52. As explained above, the QB Call Browser 154 includes several sequential screens for implementing the QB workflow.

Figure 4:
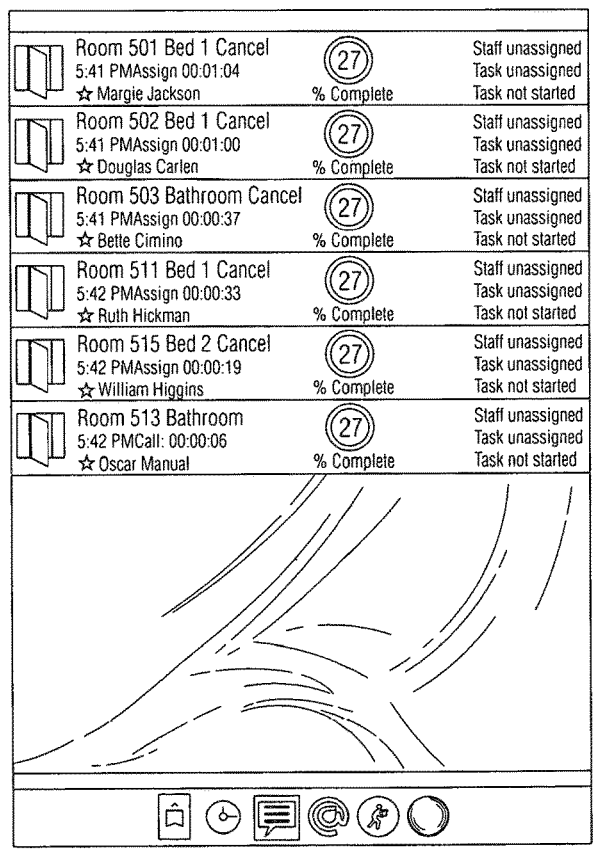
FIG. 4 is a screen sprint of the QB Call Browser 154 overview screen.

FIG. 4 is a screen sprint of the QB Call Browser 154 Overview screen, which presents a queued listing of all information regarding each queued call, including patient information (room, name), task information (reason for call), and the relevant phases: Call (time from when the patient activates the nurses call button until that call button is cancelled, steps 100-120); Assign (time from the call button cancelation until the assigned staff starts the task, steps 120-150); or Task (time it takes for the staff to complete the patient's needs, steps 150-160). A visual % progress icon is displayed at center. This same information is likewise displayed on the Staff Wear Application on staff PDAs 12.

In the context of the workflow of FIG. 2, when a patient requests assistance at step 110 the relevant information appears in the QB Call Browser overview screen. A call light icon turns red as shown in the last line item. That particular call enters the Call phase and the Call timer counts down.

The QB proceeds to the patient's room (step 120) and upon arrival deactivates the nurse call, ceasing the Call timer. This can be done using nurse call room console 44 (FIG. 2) or directly through the QB Call Browser 154 "Cancel" button. The call light icon turns white. The call enters the Assign phase and that timer begins to counts down. Note that the message in red on the top displays the status of the connection to the nurses call system. Icons at bottom provide options to create a Custom Call, Schedule Custom Call, Comment, Send an Email to appropriate staff members or department regarding the patient, Next the QB makes an initial assessment of the patient's needs (step 130), and if personally able to handle the patient's needs then such is done. However, if the QB decides further assistance is required, then at step 140 the QB application 54 Call Browser partially automates the assignment process by a succession of QB dispatcher screens and tools for real time assignment of the appropriate nurse.

Beginning at the QB Call Browser 154 Overview screen of FIG. 4, the QB views the queued listing of all information regarding each call, including patient information (room, name), task information (reasons for call), and the relevant phases: Call (time from when the patient activates the nurses call button until that call button is twill progress to display a Staff Browser to facilitate the QB's assessment of staff qualifications, location and on/off duty.

FIG. 5 is a screen print of the Staff Browser. The Staff Browser polls the location server 30 and displays each staff member's title, location, an icon of their face, and availability to begin the task (Oncall, Offline, Online). All staff members that were assigned a tag 42 are listed along with the staff member's job title and an icon indicating location within the facility (see Floor Plan below). Each staff member's unique Tag ID and Mobile ID are shown. The Tag ID is engraved on the wearable tag 42. It is used when the staff member to logs into the Staff Wear application to identify the staff member. Again, based on the foregoing task selection the QB application 54 may apply a pre-programmed ruleset to prescreen the field of candidates by comparison of each employee's qualifications relative to the selected task(s). Only qualified candidate nurses or other employees are displayed. The staff queue is sorted in priority of 1) Online/Offline; 2) RTLS location (e.g., on QB's Current Floor); 3) already Selected (Yellow Arrow pointed down indicating that staff member was already selected). "Online" means a tag 42 is detected and is in range, the RTLS location being shown. Otherwise, Offline is shown and "Out of Range" is specified for location.

The QB may tap a staff member's photo within the desired cell to select that staff member, in which case the yellow arrow changes from up to down. Up to three staff members may be assigned to a single task. This particular sequence optimizes the manner by which the assignment process is completed and also maximizes the degree to which artificial intelligence (rule-based decision making) can be brought to bear.

If the QB needs further information to make the decision they may tap once on the staff photo to engender a detail screen explaining employee task-qualifications relative to each employee based on their staff level. A double tap allows the QB to send messages (as will be described).

Figure 7:
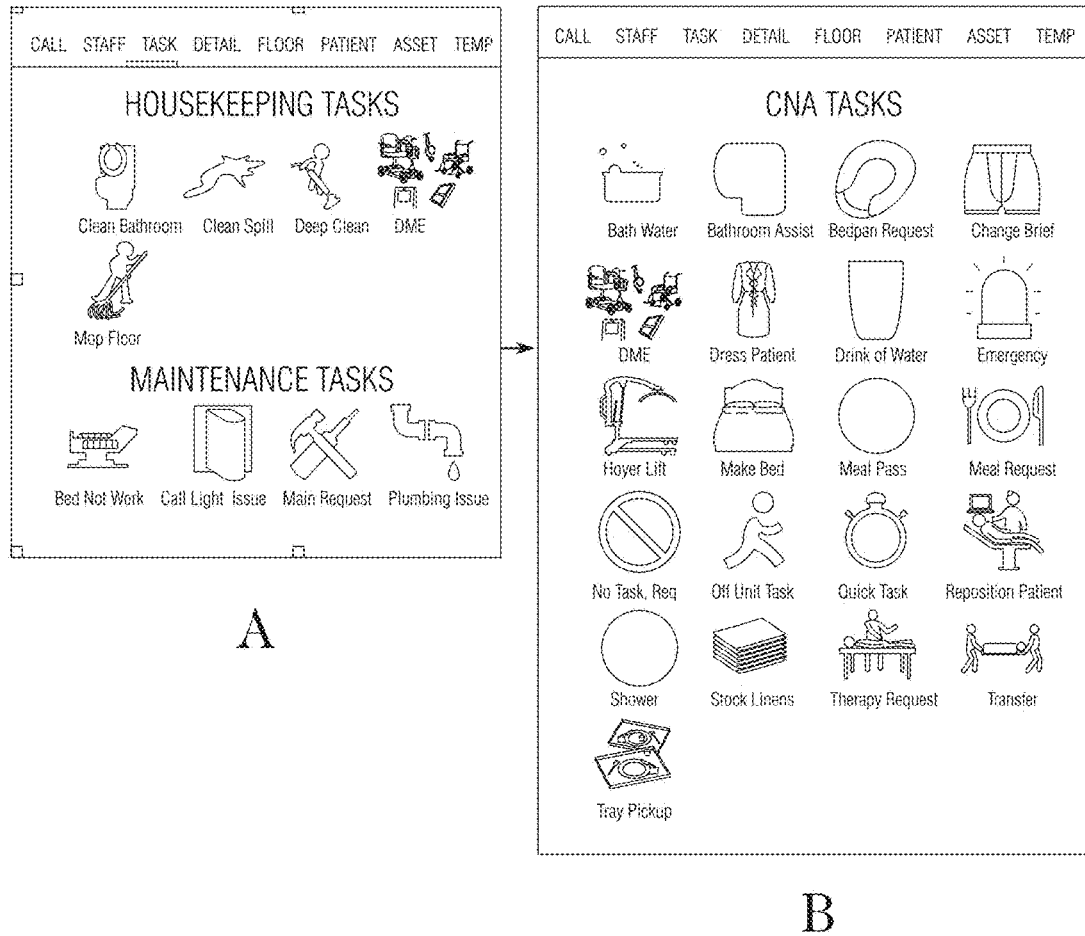
FIG. 7 is a screen print of an exemplary task list.

FIG. 7 is a screen print of an exemplary task-qualifications page, engendered by clicking on a particular staff member in the staff browser of FIG. 5. This graphically illustrates the tasks that the selected staff member is qualified to perform based on employment level relative to categorically-defined tasks. The appropriate tasks for that job position are displayed. Swiping left or right causes other Task groupings to appear. Task groups include:

CNA Tasks
    RN Tasks
    Housekeeping Tasks
    Maintenance Tasks
    Administrative Tasks (There is a No Task Required icon choice within this group)
    Kitchen Tasks Within the Task groups specific tasks appear, such as the following:

perform physical exam;
    provide counseling and education;
    administer medication;
    administer wound care;
    deliver food;
    take blood sample; etc.

The QB can select the appropriate staff member. One skilled in the art will readily understand that this process may be partially automated by ruleset comparisons that prioritize and/or foreclose certain choices.

The QB application 54 may, in an embodiment, automatically prescreen the field of candidates by comparison of each employee's qualifications relative to the selected task(s). In this case QB application 54 automatically applies a rule-based decision engine that filters candidates to complete the assigned task(s) based on the clinical requirements of the most demanding task, relative to pre-programmed employee qualifications, e.g., Registered Nurses are qualified to perform physical exams and health histories, administer medication, etc., Advanced Practice Registered Nurses are assigned specific clinical privileges, as are Nurse Practitioners, Clinical Nurse Specialists, Certified Registered Nurse Anesthetists, Licensed Practical Nurses, etc. Where multiple candidates are qualified QB application 54 may score other attributes to determine the best assignments. This way, the QB can ensure that the assignment is based on attributes or factors that best meet the task and/or patient-centric criteria. These scores may be communicated to the QB in the next screen.

Figure 6:
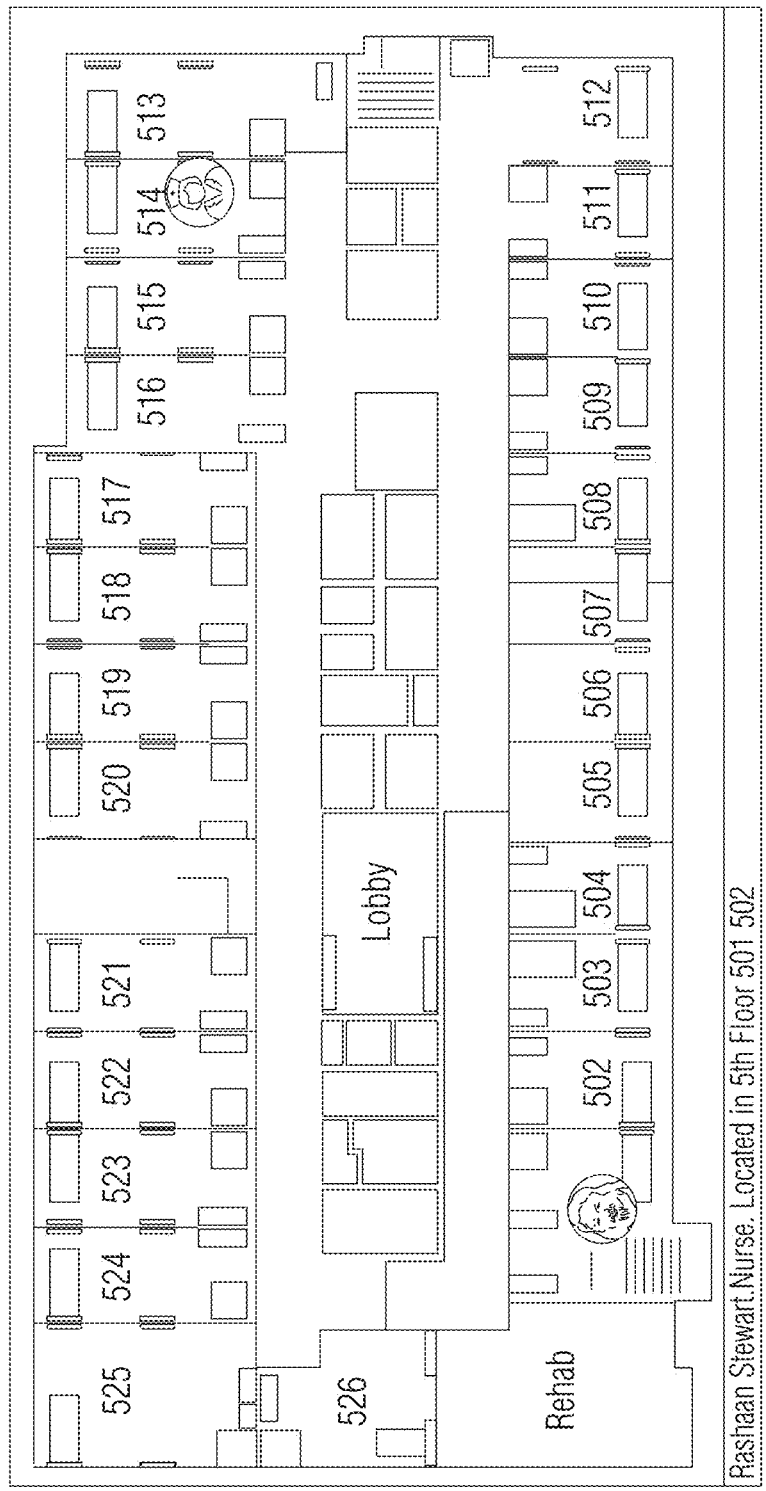
FIG. 6 is a floorplan that graphically displays each staff member's position.

The second dispatch tool shown in FIG. 6 is a floorplan that graphically displays each staff member's position by mapping a facial icon onto a floorplan map of the facility in real time. The floorplan display an icon photo of the staff member that was selected in the QB application 54, as well as other staff members selected (up arrows).

After viewing the floorplan, the QB turns back to the Staff Browser of FIG. 5 and assigns the task to the most appropriate nurse or staff member simply by clicking their facial icon (step 140). Given the nurse assignment the WFS server 14 populates the QB Call Browser 154 with the selected nurse's profile, which includes task qualifications. This allows the QB a quick visual cross-check of the assignment.

Once this is done the nurse and task assignment is communication instantly to that nurse's PDA 12, and the Assignment Timer is initiated. The task is then started. The QB may return to the QB Call Browser Overview screen. Alternately, the QB Call Browser Overview screen can be advanced to a Detail Screen.

In addition to patient-requested nurse calls, any QB or nurse may schedule a Custom Call via their respective QB Browser or Nurse Browser. This way, a nurse or QB walking by that sees a patient that requires assistance can take action. A Scheduler for custom calls is provided in the QB Browser for any patient at any time either for a single call or recurring assistance.

Figure 8:
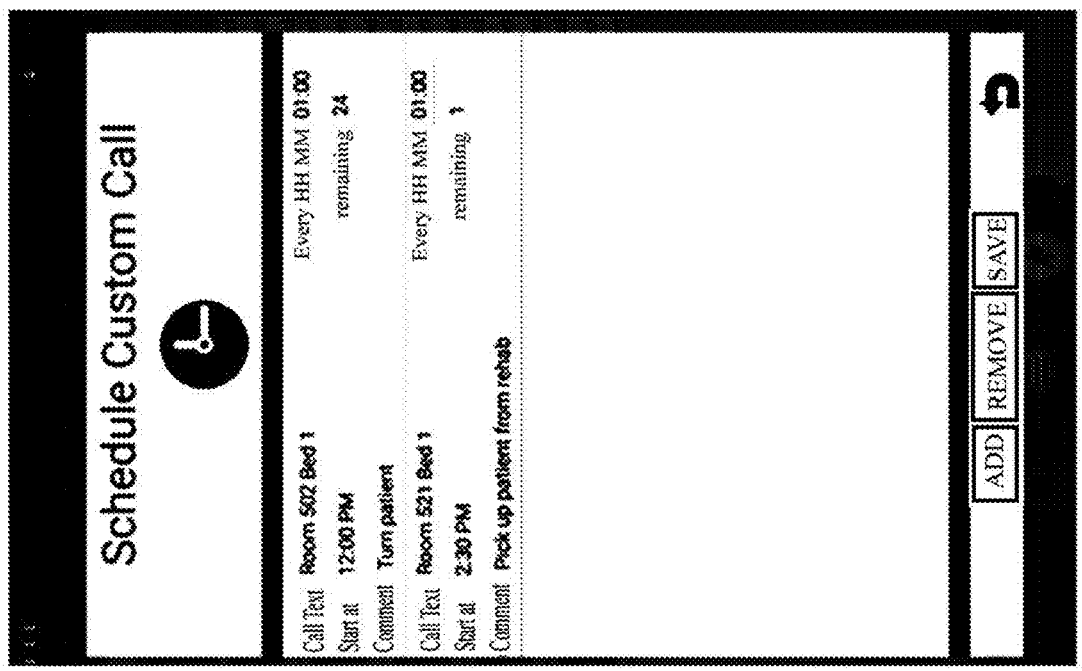
FIG. 8 is a screen shot of the Custom Call Scheduler.

FIG. 8 is a screen shot of the Custom Call Scheduler.

Figure 9:
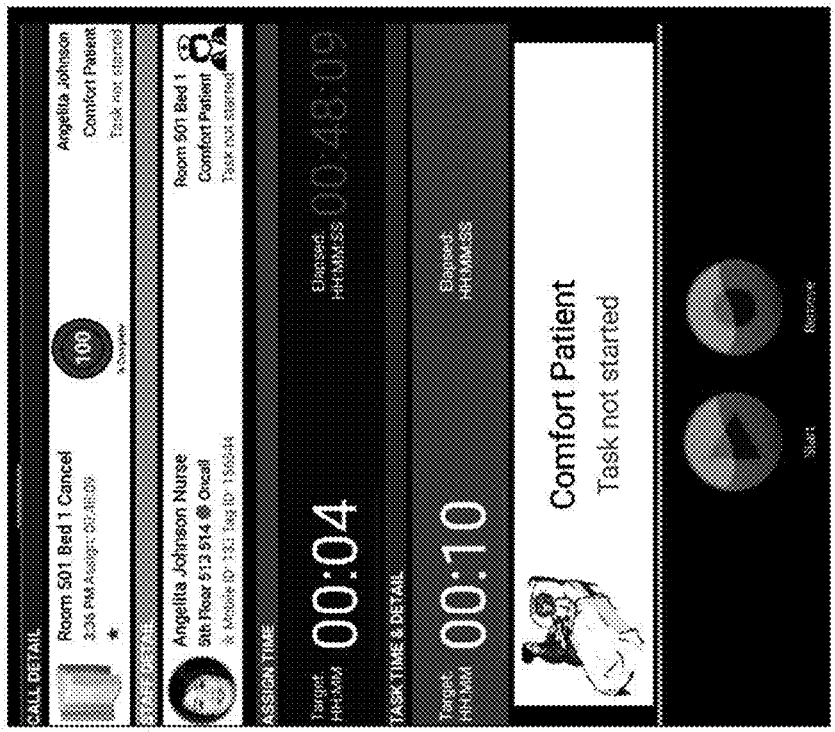
FIG. 9 is a screen print of an exemplary Detail Screen.

FIG. 9 is a screen print of an exemplary Detail Screen. The Detail Screen displays the relevant selections for that specific task. This again includes patient information (room, name), task assignment information, and both Call time (from when the patient activates the nurses call button until that call button is cancelled), and Assign Time (from the call button cancelation until the assigned staff starts the task). The remaining time required to complete the task is displayed and alarms are presented to the QB when the any times are exceeded. The nurse completes the task and removes the call from the queue (step 170) using their Staff Wear Application on PDA 12.

In addition to implementing the above-described workflow the QB application Call Browser 154 provides for additional functionality as it relates to a particular call. For one, the QB may initiate a nurse call sequence without using the patient's nurse call button, directly from the QB application 54. This allows the QB to organize nurse call notifications in advance to appear on the call browser at recurring specific times or intervals.

The QB application 54 also provides a note taking feature that allows the QB to append a comment to any selected call. The comment is archived with the call information and shown in reporting. User defined text can be inserted to alert the current and other shift QB's about special patient needs (e.g. fall status, wander risks, food allergies, distressed patient and isolation precautions etc.)

The QB application 52 also provides several enhanced communication features, including Unit Alarming and Messaging. For this the system integrates a dedicated two-way messaging platform allowing text messages (SMS) and multimedia messages (MMS) directly between predefined groups. Text messages (SMS) are used for point-to-point communication to/from the QB tablet 52 and each nurse's PDA 12. Multimedia messages (MMS) are used for unit alarming. For the latter, special SOS groups are predefined to receive multimedia messages (MMS) alarms sent from any QB tablet 52 or nurse's PDA 12. These alarms include at least the following:

1. Code Blue group: alerts everyone of code blue with location;
2. All staff on unit: alerts all staff in the unit of a general urgent assistance needed in specific location.
3. Nurse group: alerts nurses and QB on the unit of a specific need for a specific patient.

For example, there is an in-app email feature that allows the QB to send an email regarding the selected call to department heads or another management staff. This initiates conversation between the QB and department heads so they are aware of follow up for a specific task.

There is an in-app Quarterback to Quarterback messaging feature that allows the QBs to reach out to other QB's in the facility to request additional staff support.

There is also a Code Blue Alert Feature to alert other QBs and staff members of an emergency code blue.

The QB application 54 also provides access to several other browsers for implementing the QB workflow.

For example, there is a Patient Browser that gives the QB quick access to important patient medical information. This information comes from the EHR/patient care database 35 (FIG. 2).

Tracking tags 42 may also be mounted on equipment (as opposed to nurses) and the QB application assigns an asset ID code to separately track these asset tags 42. Server 30 associates the unique ID data from the tags 42 with asset data, such as a serial number, of the corresponding Hoyer Lift.

Figure 10:
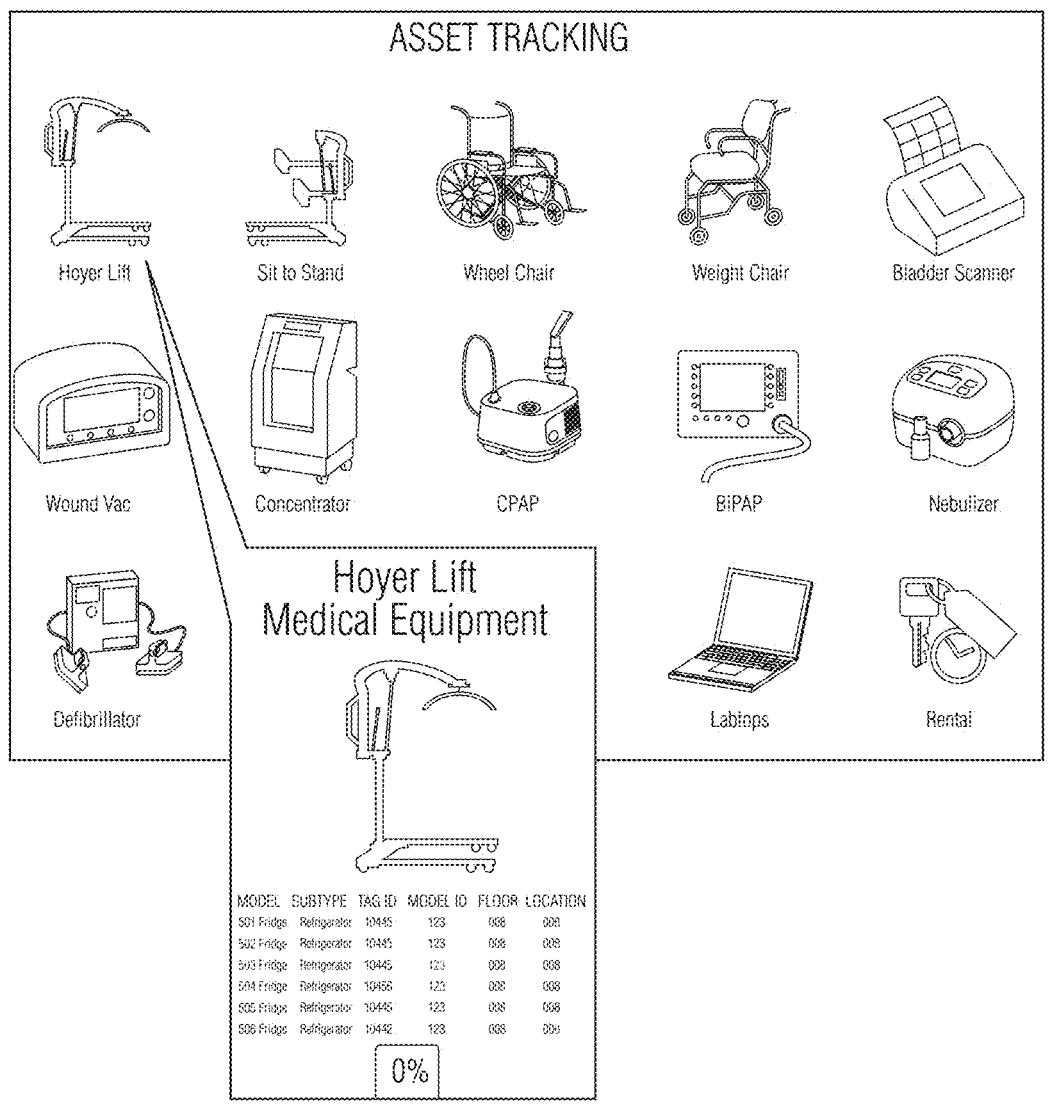
FIG. 10 is a screen print of the Asset Tracking Browser.

FIG. 10 is a screen print of the Asset Tracking Browser, which generally comprises a menu of icons each representing a class of asset. Any icon can be clicked to provide a listing of all site assets within that category (name, model, tag UD, serial number, and location by floor and room). This allows quick location of any asset by category. When there are multiple assets of the same type, each will be listed with their floor and location. Quick location of medical devices allows staff to perform tasks in a time efficient method. It also protects against theft and provides instant inventory accounting.

There are also special-purpose temperature tracking tags 42 to monitor the temperature of rooms or assets. When a temperature falls outside of a predetermined range, an alarm and email is automatically sent do the appropriate staff member or department. Refrigerator alarms are sampled multiple times before sending and alarm to avoid false alarming each time the fridge is opened.

Figure 11:
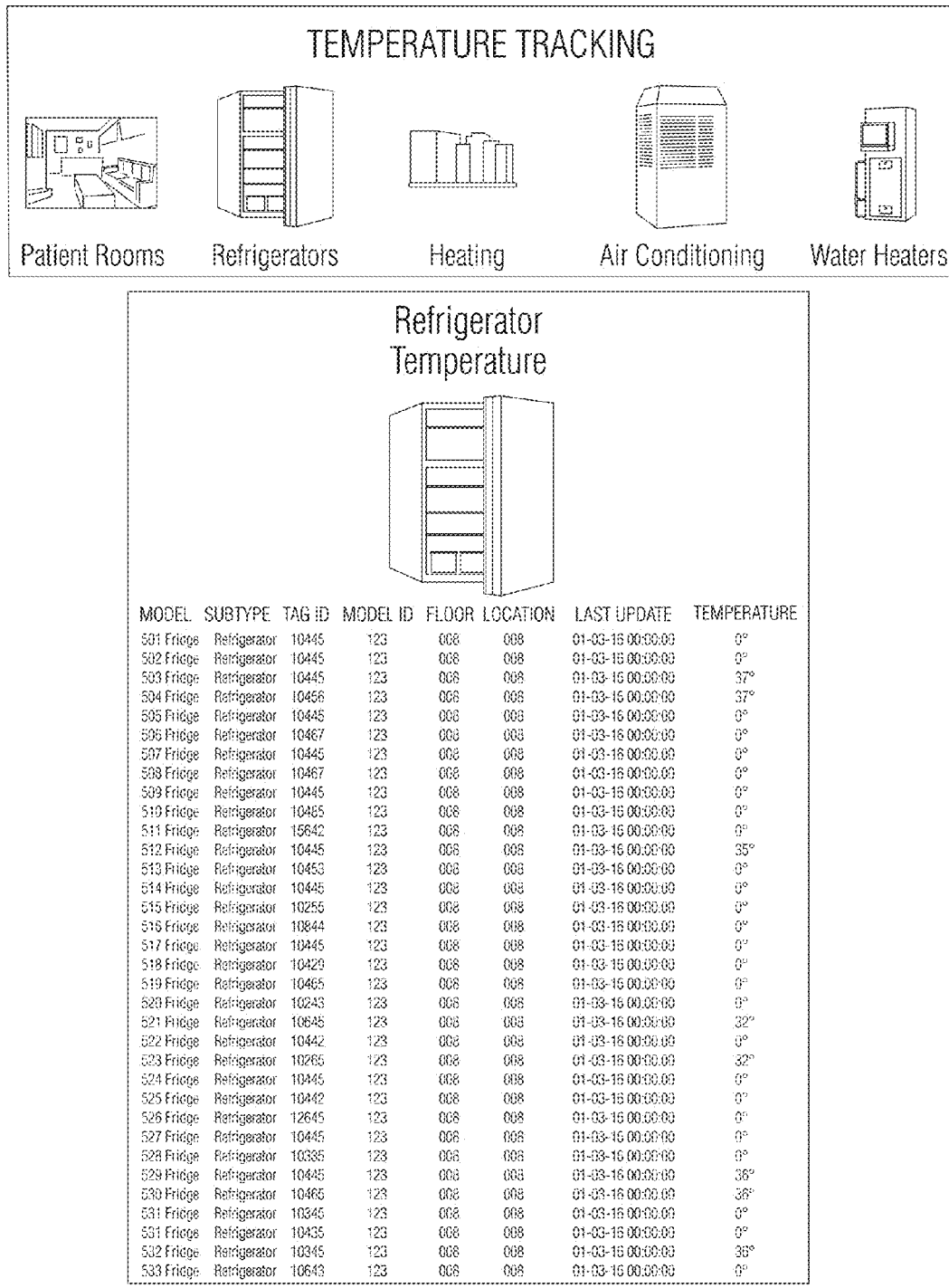
FIG. 11 is a screen print of the Temperature Tracking Browser.

FIG. 11 is a screen print of the Temperature Tracking Browser, which generally comprises a menu of icons each representing something for which the temperature is being monitored, e.g., a refrigerator. Any icon can be clicked to provide a detailed listing of all assets within that category for which temp is being tracked (name, model, tag UD, serial number, and location by floor and room). This allows quick location of any asset by category.

The QB application 52 also provides a Schedule Module that display the facility general schedule and the QB's personal schedule including therapy appointments, medication and treatment time ranges, meal times, event times, appointments, etc.

The QB application 52 also provides an Endorsement Tool that formalizes the process of shift to shift endorsement (update and warm handoff) of pertinent concerns regarding imminent and upcoming patient needs.

Similar to the QB tablet 52 which executes a QB software application 54 as described above, patients may also be provided with a patient tablet 66 running a patient application 68 in wireless communication with nurse call server 14 and in communication with hospital network 20. The patient tablet is preferably a 6" or 8" touchscreen tablet tethered to the bed in a manner similar to a traditional nurse call button, housed in a custom protective case, and powered from a standard wall socket or from the existing nurse's wall mounted call box. The patient application 68 is crash proof (when the tablet 66 restarts it reloads automatically). The patient tablet 66 and application 68 provides for traditional nurses call and cancel functionality, and is intended to provide an alternative to the traditional nurse call button. Toward that end it instantiates to a Patient Browser which displays large CALL and CANCEL buttons, and allows the patient to indicate the reason of the call. This allows the QB to assign most tasks without coming to the room. In addition, the QB respond to the patient's request, e.g., "your pain medication is on the way." The patient application 68 displays the Call Timer and Assign Timer, and as soon as a call is made the application starts counting down based on the system set expected initial response time. These timers may be extended manually by the QB when the situation is appropriate, for purpose of giving the patient the benefit of notification that it will take a bit more time. As above, the patient tablet also has integrated communication (voice, text, video) with the QB who can interact with the patient right away, possibly allowing some nurse calls to be moved to the Assign phase right away. Note that the interactivity of the patient tablet 66 allows a fully remote implementation of the Quarterback, such that the QB may be remotely located in the administration department or even at home. The nurse call sequence is slightly modified from that described above as follows:

1. Patient presses CALL button on Patient Browser 68;
2. QB responds through the tablet 66 itself and asks the patient what is required (Call phase);
3. Remote QB determine how long it will take to have the closest and available staff member attend to the patient's needs and informs the patient. The patient application 68 displays estimated remaining time;
4. QB finds the appropriate staff member and assigns the task as above.
5. The assigned staff member gets notification through their Staff Wear device of a task pending (Assign Phase).
6. The staff member (or QB) starts the task. (Task Phase)
7. The staff member sees a counter on the wear device showing remaining time for the Task Phase. The QB sees the same timer.
8. If the staff member requires additional time, he/she taps their Staff Wear device. This is reflected in the QB tablet 52 as well as the patient's estimated time on their tablet 66.
9. When the task is completed, the staff member presses Complete on their Staff Wear device.
10. QB can follow up with the patient if desired.

The patient application 68 also includes a Schedule Module as for the patient's scheduling as described above, and a Solution Center module that allows the patient to send questions and communication requests directly to various departments. It preferably also incorporate features to allow patients, family and friends to directly communicate with each other. Using the patient tablet 66 with patient application the patient can accomplish the following:

Order from a selected menu based on dietary needs.
View and add information to their Patient Schedule Module.
Request support from Guest Services.
Make Service requests (food, beauty shop, massage, physician request, etc.)
Schedule appointments
Sign up for Activities
Schedule Activities
Maintain a Therapy Schedule
Submit a patient evaluation for feedback.
Receive periodic event notifications thus providing for an exceptional patient experience, e.g., dinner will be served in 15 minutes.

The Staff Wear Application similarly provides for tracking tasks and providing communications between the QB's and other staff members, and Code Blue Facility and Unit alarming, as well as a Nurse Request function (described below when, for example, a staff member requires a nurse to immediately access or address an urgent issue with a patient). The Staff Wear Application can be installed on any smart device 12 (FIG. 2). The Staff Wear Application is preferably programmed in Android Wear 2.0, and is similar to the QB Application Browser 54 but made to display limited information per screen. The different screens include the following:

Task Page: for staff to see their task assignments and indicate task is completed;
A count down timer for the current task;
QB location;
two-way communication with specific buttons for each staff member and an emergency button to communicate to all staff.

In addition to the QB Tablet 52, a room door tablet 56 may be mounted outside each room, and run a Room Door Tablet Application 58 connected to the facility WAN or network 20 to provide the most recent patient information shown in real time. The default display includes Room Number, Patient Name, Patient Isolation Flag, Patient Fall Risk Flag, Discharged, Deep Clean Required Flag, Ready For Inspection Flag, Room has Been Inspected Flag, and Room Change in Progress Flag. The room door tablet 56 enables smoother transitions during admissions, discharges and room changes. The Room Door Tablet Application 58 is likewise a web-based thin client front end that allows administration staff to send message flags to the door tablets, display the status of each tablet by room number in real-time. The Room Door Tablet Application 58 is tightly integrated with the QB application and Staff Wear application. Thus, for example, a code blue alarm will cause a distressed patient's Room Door Tablet Application 58 to flash critical information and audio messaging. Other Room Door Tablet Applications 58 may display graphic arrows pointing in the direction of the emergency.

As indicated above all statistical data regarding Call (time from when the patient activates the nurses call button until that call button is cancelled, steps 100-120), Assign (time from the call button cancelation until the assigned staff starts the task, steps 120-150), and Task (time it takes for the staff to complete the patient's needs, steps 150-160), is archived for reporting and compiled into a variety of informative management reports as follows:

Call Summary Report

This report is a displays all the Call, Assign, and Task time detail for calls for a selected date range. FIG. 11 is a screen print of an exemplary Call Summary Report. A Call Time Threshold is used to determine over-time indications by using different colors. A graphical summary data is available at the end of the report.

Call Detail Report by Date and Time Range

This is an ad hoc report will list the details of each call by timestamp and include all details about all calls within a date time range. Call details include: Room; Bed; Call Time; Assign Time; Task Time; Resident Name; Patient ID EMR; Quarterback Name; Staff Assigned To Name(s); Staff Assigned To Position(s) (CNA, RN, etc.); Comment Text; Email Sent Flag; and Custom Call Flag.

Call Detail Report by Room & Bed Number

This report lists the details of each call by timestamp for each room and bed for a selected date and time period. This allows for a detailed review of the quality of care offered to a patient.

Call details include: Room, Bed, Call Time, Assign Time, Task Time, Resident Name, Patient ID EMR, Quarterback Name, Staff Assigned To Name(s), Staff Assigned To Position(s) (CNA, RN, etc.), Comment Text, Email Sent Flag, Custom Call Flag.

Detail Report by Quarterback

This report displays call, assign, and task time by individual QB for a selected time period. A Call Time Threshold is used to determine over-time indications by using different colors. A summary score is provided for each QB to be used for comparison and for performance evaluation.

Detail Report by Staff Member Response

This report displays the task time by Staff Member for a selected time period. A Call Time Threshold is used to determine over-time indications by using different colors. A summary score is provided for each staff member to be used for comparison and for performance evaluation.

It should now be apparent that the above-described invention provides an improved dispatch management system for workflow optimization of the patient-nurse call process, that integrates with existing healthcare provider client-server networks hosting a medical records database. The dispatch management system increases the level of automation of the nurse dispatch process, facilitates more efficient deployment of provider staff, and fully tracks and produces a new set of metrics for more efficient management and oversight of provider staff. In addition, the system maintains an audit trail throughout the nurse call process.

This has been a description of the present invention and, the preferred embodiment of the present invention, as well as various alternate embodiments of the present invention.

We claim:

1. A dispatch management system for workflow optimization of the patient-nurse call process, said dispatch management system being integrated with an existing healthcare provider client-server network including a computer network in communication with a medical records database and a nurse call system, the dispatch management system comprising:
   a plurality of real-time location service (RTLS) tracking tags each identified by a unique identification code, each assigned to a nurse, and each periodically transmitting a message at least including said unique identification code and location information;
   an RTLS location server in communication with said healthcare provider client-server network, said RTLS location server comprising a computer having non-transitory computer memory connected to said healthcare provider client-server network, said RTLS location server running application software comprising computer instructions stored on said non-transitory computer memory for tracking a real time position of each of said RTLS tracking tags;
   a nurse call server in communication with said healthcare provider client-server network, said nurse call server comprising a computer having non-transitory computer memory connected to said healthcare provider client-server network, said nurse call server running application software comprising computer instructions stored on said non-transitory computer memory for maintaining a database of nurses and associated identification codes, and for querying said RTLS location server to determine a position of said nurses within a facility;
   a portable quarterback (QB) computer in communication with said nurse call server, said portable QB computer connected to said healthcare provider client-server network, said portable QB computer running a QB computer application for displaying a QB Call Browser comprising a plurality of screens inclusive of an overview screen presenting a nurse call cancellation button, a task selection screen comprising a listing of categorical tasks selectable for assignment to a designated nurse, and a queued listing of all requested nurse calls including patient room, name, reason for call, said QB Application further comprising a timer for tracking time to completion of at least three stages of each nurse call inclusive of Call Time from when a patient activates a nurses call button until actuation of the nurse call cancellation button, an Assign Time from said cancellation actuation until an assigned nurse begins an assigned task, and Task Time for the assigned nurse to complete the assigned task;
   a plurality of mobile devices each identified by a unique identification code and each assigned to a nurse, each mobile device being connected to said nurse call server, and each mobile device comprising a computer running application software comprising a Nurse Browser for remotely displaying a subset of information displayed on said QB Call Browser, said QB Call Browser deactivates said Call Time timer and activates said Assign Time timer when said QB assigns a task to the assigned nurse, said Nurse Browser including a control for accepting a QB assigned task by the assigned nurse, and said QB Call Browser displays an instant notification when said assigned nurse actuates said control to accept a QB assigned task.

2. The dispatch management system according to claim 1, wherein said Nurse Browser displays an instant notification when said QB assigns a task to the assigned nurse.

3. The dispatch management system according to claim 1, wherein said QB Call Browser deactivates said Assign Time timer and activates said Task Time timer when said assigned nurse actuates said control to accept a QB assigned task.

4. The dispatch management system according to claim 3, wherein said Nurse Browser includes a control for indicating completion of a QB assigned task by the assigned nurse.

5. The dispatch management system according to claim 4, wherein said QB Call Browser displays an instant notification when said assigned nurse actuates said control to indicate completion of a QB assigned task.

6. The dispatch management system according to claim 5, wherein said QB Call Browser deactivates said Task Time timer when said assigned nurse actuates said control to indicate completion of a QB assigned task.

7. The dispatch management system according to claim 1, wherein said QB Call Browser displays an assignment page listing only qualified candidates for completion of a selected task.

8. The dispatch management system according to claim 1, wherein said QB Call Browser displays a floorplan page comprising a map of a facility and a real time position of a plurality of nurses determined from said RTLS location server.

9. The dispatch management system according to claim 8, further comprising a plurality of RTLS tracking tags each identified by a unique identification code, each assigned to an asset, and each periodically transmitting a message at least including said unique identification code.

10. The dispatch management system according to claim 8, wherein said QB Call Browser displays an asset page comprising real time position of each assigned asset determined from said RTLS location server.

11. The dispatch management system according to claim 1, wherein at least some of said RTLS tracking tags periodically transmits temperature.

12. The dispatch management system according to claim 1, wherein said RTLS location server application software comprises computer instructions stored on said non-transitory computer memory for tracking a real time position of each of said RTLS tracking tags by at least two from the group consisting of trilateration, fingerprinting and proximity sensing.

13. The dispatch management system according to claim 1, wherein said RTLS tracking tags periodically transmit Bluetooth low energy beacons.

14. A dispatch management system for workflow optimization of the patient-nurse call process, said dispatch management system being integrated with an existing healthcare provider client-server network including a computer network in communication with a medical records database and a nurse call system, the dispatch management system comprising:
- a plurality of real-time location service (RTLS) tracking tags each identified by a unique identification code, each assigned to a nurse, and each periodically transmitting a message at least including said unique identification code and location information;
- an RTLS location server in communication with said healthcare provider client-server network, said RTLS location server comprising a computer having non-transitory computer memory connected to said healthcare provider client-server network, said RTLS location server running application software comprising computer instructions stored on said non-transitory computer memory for tracking a real time position of each of said RTLS tracking tags;
- a nurse call server in communication with said healthcare provider client-server network, said nurse call server comprising a computer having non-transitory computer memory connected to said healthcare provider client-server network, said nurse call server running application software comprising computer instructions stored on said non-transitory computer memory for maintaining a database of nurses and associated identification codes, and for querying said RTLS location server to determine a position of said nurses within a facility;
- a portable quarterback (QB) computer in communication with said nurse call server, said portable QB computer connected to said healthcare provider client-server network, said portable QB computer running a QB computer application for displaying a QB Call Browser comprising a plurality of screens inclusive of an overview screen presenting a nurse call cancellation button, a task selection screen comprising a listing of categorical tasks selectable for assignment to a designated nurse, and a queued listing of all requested nurse calls including patient room, name, reason for call, said QB Application further comprising a timer for tracking time to completion of at least three stages of each nurse call inclusive of Call Time from when a patient activates a nurses call button until actuation of the nurse call cancellation button, an Assign Time from said cancellation actuation until an assigned nurse begins an assigned task, and Task Time for the assigned nurse to complete the assigned task;
- a plurality of mobile devices each identified by a unique identification code and each assigned to a nurse, each mobile device being connected to said nurse call server, and each mobile device comprising a computer running application software comprising a Nurse Browser for remotely displaying a subset of information displayed on said QB Call Browser;
- a portable Room Door computer in communication with said nurse call server, said portable QB computer connected to said healthcare provider client-server network, said portable Room Door computer running a Room Door computer application for displaying patient information in real time, wherein said patient information at least includes Room Number, Patient Name, Patient Isolation Flag, Patient Fall Risk Flag, Discharged, Deep Clean Required Flag, Ready For Inspection Flag, Room has Been Inspected Flag, and Room Change in Progress Flag.

15. In combination with a legacy nurse call system in communication with a hospital computer network for allowing healthcare patients to summon healthcare staff, a system for nurse call dispatch workflow optimization, comprising:
- a nurse call server computer;
- an interface to said legacy nurse call system configured to notify said nurse call server computer when a patient makes a nurse call to said legacy nurse call system;
- a real-time location service (RTLS) computer server in communication with a plurality of tracking tags, some of said plurality of tracking tags being worn by said healthcare staff;
- a plurality of personal digital assistants (PDAs) each being worn by a respective member of said healthcare staff, each in communication with said nurse call server computer, and each PDA having non-transitory computer memory running a staff wear application comprising computer instructions stored on the non-transitory computer memory for executing the treatment plan;
- a portable quarterback (QB) computing tablet assigned to a supervisory member of said healthcare staff, said QB tablet being in communication with said nurse call server and all of said plurality of PDAs, and said QB tablet having non-transitory computer memory running a QB application comprising computer instructions stored on the non-transitory computer memory for compiling an assessment of patient needs when said interface notifies said nurse call server computer when a patient makes a nurse call to said legacy nurse call system and display the assessment on the QB tablet inclusive of room and bed number, timestamp, time elapsed between QB cancellation of said nurse call and staff assignment, and time elapsed for attending the call, wherein said QB application displays a QB browser with a control to deactivate the nurse call, a timer to track lapsed time between initiation and deactivation of the nurse call, and provides an alarm if said lapsed time between initiation and deactivation of the nurse call exceeds a predetermined threshold, and wherein said QB application provides a dispatch screen with controls allowing said supervisory staff member to assign said nurse call to any one of said plurality of healthcare staff members, displays a timer to track lapsed time between QB cancellation of said nurse call and staff assignment, and provides an alarm if said lapsed time between QB cancellation and staff assignment exceeds a predetermined threshold; and wherein said QB application is configured to send an alert to that PDA in custody of the staff member to whom the nurse call is assigned via said QB browser, and said staff wear application is configured to emit the alert to said assigned staff member upon receipt of said alert.

16. The system for nurse call dispatch workflow optimization according to claim 15, wherein said QB application and said staff wear application display a timer to track lapsed time between assignment of said initiation and deactivation of the nurse call.

17. The system for nurse call dispatch workflow optimization according to claim 15, wherein said staff wear application comprises a control for allowing said assigned staff member to cancel said nurse call upon visiting said patient's room.

18. The system for nurse call dispatch workflow optimization according to claim 16, wherein said QB application and said staff wear application display a timer to track lapsed time between staff assignment and cancellation of said nurse call.

19. The system for nurse call dispatch workflow optimization according to claim 18, wherein said QB application provides an alarm if said lapsed time between staff assignment and cancellation of said nurse call exceeds a predetermined threshold.

20. A method for nurse call dispatch workflow optimization, comprising the steps of:
providing a nurse call server computer;
providing an interface to a legacy nurse call system configured to notify said nurse call server computer when a patient makes a nurse call to said legacy nurse call system;
providing a real-time location service (RTLS) computer server in communication with a plurality of tracking tags, and assigning each said tracking tag to be worn by one of said healthcare staff;
providing each of said healthcare staff with a personal digital assistant (PDA) in communication with said nurse call server computer, and each PDA having non-transitory computer memory running a staff wear application comprising computer instructions stored on the non-transitory computer memory for executing the treatment plan;
providing a supervisory staff member with a portable quarterback (QB) computer tablet in communication with said nurse call server and all of said plurality of PDAs, said QB tablet having non-transitory computer memory running a QB application comprising computer instructions stored on the non-transitory computer memory for compiling an assessment of patient needs when said interface notifies said nurse call server computer when a patient makes a nurse call to said legacy nurse call system;
displaying the assessment on the QB tablet inclusive of room and bed number, timestamp, and time elapsed for attending the call;
displaying a dispatch screen on said QB computer tablet with controls allowing said supervisory staff member to assign said nurse call to any one of said plurality of healthcare staff members;
displaying a control on said QB computer tablet to deactivate the nurse call; and
displaying a timer to track lapsed time between initiation and deactivation of the nurse call;
emitting an alarm if said lapsed time between initiation and deactivation of the nurse call exceeds a predetermined threshold;
displaying a control on said PDA to cancel the nurse call;
displaying a timer to track lapsed time between PDA cancellation of said nurse call and staff assignment; and
emitting an alarm if said lapsed time between PDA cancellation and staff assignment exceeds a predetermined threshold.

21. The method for nurse call dispatch workflow optimization according to claim 20, further comprising a step of sending an alert to that PDA in custody of a staff member to whom a nurse call is assigned via said QB browser.

22. The method for nurse call dispatch workflow optimization according to claim 20, further comprising a step of tracking lapsed time between assignment of said initiation and deactivation of the nurse call, and emitting an alarm if said lapsed time exceeds a predetermined threshold.

23. The method for nurse call dispatch workflow optimization according to claim 20, wherein said staff wear application comprises a control for allowing said assigned staff member to cancel said nurse call upon visiting said patient's room.

24. The method for nurse call dispatch workflow optimization according to claim 20, further comprising a step of tracking lapsed time between staff assignment and cancellation of said nurse call, and emitting an alarm if said lapsed time between staff assignment and cancellation of said nurse call exceeds a predetermined threshold.

25. The method for nurse call dispatch workflow optimization according to claim 20, further comprising a step of displaying a listing of all staff members wearing one of said tracking tags and in range of said RTLS computer server.

26. The method for nurse call dispatch workflow optimization according to claim 20, further comprising a step of displaying a floorplan indicating location of all staff members wearing one of said tracking tags and in range of said RTLS computer server.

* * * * *